(12) United States Patent
Jimenez

(10) Patent No.: US 7,037,562 B2
(45) Date of Patent: May 2, 2006

(54) ANGIOPLASTY SUPER BALLOON FABRICATION WITH COMPOSITE MATERIALS

(75) Inventor: Oscar Jimenez, Coral Gables, FL (US)

(73) Assignee: Vascon LLC, Miami, FL (US)

( * ) Notice: Subject to any disclaimer, the term of this patent is extended or adjusted under 35 U.S.C. 154(b) by 0 days.

(21) Appl. No.: 10/046,452

(22) Filed: Jan. 14, 2002

(65) Prior Publication Data

US 2003/0143350 A1 Jul. 31, 2003

(51) Int. Cl.
 *B29D 22/00* (2006.01)
 *B29D 23/00* (2006.01)
 *B32B 1/08* (2006.01)

(52) U.S. Cl. .................. 428/36.4; 428/35.7; 428/34.5; 428/408

(58) Field of Classification Search ............... 428/35.7, 428/34.5, 36.4, 408; 623/1.15; 606/194, 606/198, 200
See application file for complete search history.

(56) References Cited

U.S. PATENT DOCUMENTS

2003/0065355 A1* 4/2003 Weber .................. 606/200
2003/0229184 A1* 12/2003 Acquarulo et al. ......... 525/505

FOREIGN PATENT DOCUMENTS

WO   WO 01/34685       5/2001
WO   WO 01/34685 A1 *  5/2001

\* cited by examiner

*Primary Examiner*—Michael C. Miggins
(74) *Attorney, Agent, or Firm*—Thomas R. Vigil; Welsh & Katz, Ltd.

(57) ABSTRACT

The balloon catheter comprises a plastic tubing, a balloon fused to one end portion of said tubing, and the balloon being made of a polymer and one of a carbon nano-tube material, a nano-clay material or a nano-ceramic fiber material.

13 Claims, No Drawings

ANGIOPLASTY SUPER BALLOON FABRICATION WITH COMPOSITE MATERIALS

BACKGROUND OF THE INVENTION

1. Field of the Invention

The present invention relates to reinforced balloons and to several methods for creating composite films of organic polymers and inorganic additives on a nanometric scale which are compounded with polymers to be used to form angioplasty ballons to increase their strength. The super balloons or reinforced balloons are created with carbon nanotubes, clay platelets or ceramic, e.g. alumina, fibers which are included in the balloon material with a polymer.

Angioplasty balloons are required to be able to withstand very high pressures, which force the balloon's surface against various vessel tissues and deposits representing a range of viscoelastic characteristics, and include some very hard and rough surfaces. As the balloons must be thin-walled to collapse into a small profile (cross-section) for introduction to the target area, the balloons must be made extremely strong and puncture resistant. The balloons also must expand in a predictable manner when the internal pressure is beyond the nominal value where the cross-section is rated. In addition, balloon catheters are also used to deploy metallic stents within a constricted vessel. Stents are expandable wire or flat metal mesh devices that help retain proper vessel lumen after dilation. In this application, the balloon must come in contact with a metallic mesh that may inflict damage to the balloon. To meet these exacting requirements the present invention teaches several methods of creating composite films of organic polymers and inorganic additives, including carbon nanotubes, nanoclays, and ceramic, alumina, fibers on a nanometric scale. The invention is also directed at the preparation and formation of balloons using specifically carbon nanotubes, clay platelets and ceramic fibers.

2. Description of the Prior Art

Angioplasty addresses the problems related to partially or fully obstructed blood vessels. Angioplasty balloons have been used by invasive cardiologists since the 1970s when Andreas Grunzig reported his data on reopening the occluded coronary arteries of five patients and that these arteries remained patent, open, allowing blood flow for six months or longer. The Grunzig procedure involved the introduction of a high-pressure angiographic catheter with a deflated or collapsed polymer balloon attached to its distal portion. Once the catheter is positioned within the occluded range (lesion) in the artery under fluoroscopic control, the balloon is pressurized, typically by injecting a fluid. The pressure in the balloon exerts pressure on the surrounding obstructive structures and enlarges the lumen, which results in an increase in blood flow.

Subsequently, the balloon is depressurized until it collapses and it then can be withdrawn from the obstructed site where circulation has been restored through this maneuver.

As angioplasty, the reforming of blood vessels, has gained acceptance and replaced to a great extent the conventional coronary artery bypass graft procedure, a major surgical intervention, the demands for the performance of the balloon catheter have increased. These demands include high strength balloons to withstand pressures on the order of 10 to 20 atmospheres. In comparison, the typical passenger car's tires are inflated to about 32 psi or slightly above 2 atm. above the ambient pressure. While the typical tire wall is a composite, the walls are reinforced by high strength weaves of polyester filaments or stainless steel wires embedded in a visco-elastic matrix, such as neoprene, the typical angioplasty balloon is made of a polymer film with its wall thickness in the vicinity of 0.001" or 25 micrometers. Thus the stress in the angioplasty balloon is determined to be about ten times higher internal pressure in a wall that is about one two hundredth thick, hence its stress is estimated to be 2000 times greater than in a tire. Both tires and balloon catheters encounter similar excess strain when they press against sharp objects. Automobile tires are usually designed to be puncture-proof when being pressed against a sharp nail; they are to allow the metal tip to penetrate while forming at least a temporary seal around it. The balloon catheter's wall may be exposed to the sharp edges of crystalline deposits. The ratio of the wall's thickness to the length of the puncturing object is much more favorable for the tire than for the angioplasty balloon, hence the balloon must exhibit great resistance to cuts by the sharp edges of the crystalline deposit in a plaque, the obstructive body in the vessel. Thirdly, both the automobile tire and the angioplasty balloon must be able to withstand overinflation without excessive plastic flow or rupture. In case the plaque to be broken by the inflated balloon is hard, dense and strong, the physician often attempts to inflate the balloon above its nominal pressure to increase the balloon's diameter in a predictable manner. For such events it is important to know the relationship between the desired additional diameter for the balloon above the rated value and the pressure necessary to achieve that.

When monomers in the general family of amides are polymerized to form polyamides, or Nylons, the strength of the balloon made from such materials is usually not isotropic, because the polymer chains are oriented to be parallel to the axis of the inflated balloon. The reason for this is rooted in the way the balloon is designed to fail in case it is overinflated beyond its failure stress level. The balloon is expected to split parallel to the catheter's axis to enable the withdrawal of the fractured balloon without leaving any portion behind. Such debris would typically require surgical removal that is possibly as traumatic as the bypass procedure that the angioplasty was expected to avoid.

The balloons, unlike tires, must also have lubricious surfaces and must be chemically inert. Polyamide or Nylon films generally meet these requirements.

Films made with certain polymer films containing either carbon nanotubes or clay platelets offer greater strength for the balloon without sacrifice of the viscoelastic properties necessary for over-inflation.

Carbon nanotubes were discovered by accident by Sumio Iijima, in 1991, in soot. Their properties have been studied extensively and the strength, flexibility and conductivity of the individual nanotubes have been measured with remarkable results. While singly, the nanotubes, characterized by approximately one nanometer diameter ($10^{-9}$ m or 0.001 micrometer) have found few practical uses, they have been considered as the high strength component in composite materials. The physical characteristics of long nanotubes, which may reach a micrometer in length, suggest their use for conducting elements between semiconductor gates. Electron microscopists have observed carbon nanotubes with single or multiple but concentric cylindrical walls.

One of the factors which have delayed the use of nanotubes in composite materials is their extremely high cost. Some of this cost is associated with the difficulties in producing the nanotubes, typically from arc discharges. Another reason for the high cost is that often the electronic application requires a degree of uniformity in tube length and in the number of layers. The cost of a gram of uniform nanotubes has been in the range of $100 to over $1000. While this cost is a deterrent, the quantities of nanotubes needed for the manufacturing of angioplasty balloons are very small. For instance, a typical balloon may have 25 micrometer wall thickness and an equivalent diameter of 3 mm and length of 30 mm. The volume of material in such a balloon is merely 7 mm$^3$. Further assuming that the volume ratio of carbon nanotubes to the volume of material is not more than 0.3, the volume of carbon nanotubes required is about 2 mm$^3$. The mass of carbon in the balloon, assuming that the density is about 2 grams/cm$^3$, is about 4 milligrams and its direct cost at $100 per gram is $0.40 per balloon.

As the cost of producing carbon nanotubes is declining, the composite material is economically practical in such demanding and relatively cost insensitive applications as coronary angioplasty.

Balloon fabrication has been extensively addressed in a number of US patents. For example, U.S. Pat. No. 5,868,704 Balloon Catheter Device (Issue date: Feb. 9, 1999, filing date, Jun. 26, 1996) by Campbell, Laguna and Spencer, assigned to W. I. Gore & Associates, describes composite balloon materials where the components are polymers, typically porous polytetrafluoroethylene (PTFE) films combined with an elastomer to achieve some of the properties described above. One particular embodiment involves helically wound ribbons progressing in opposite directions to each other with specific pitch between the adjacent turns of the ribbon. The layers are thermally bonded to each other.

U.S. Pat. No. 5,506,049 of Swei and Arthur, assigned to Rogers Corp. is titled Particulate Filled Composite Film and Method of Making Same, and teaches the fabrication of films made with fluoropolymers filled with small particles for use as dielectric substrates.

U.S. Pat. No. 4,330,587 of Woodbrey, assigned to Monsanto Co. is titled Metal-Thermoplastic-Metal Laminates, teaches the fabrication of films which may be formed easily and exhibit high tensile strength. The core layer is polyamide or polyester sandwiched between aluminum alloy layers. This patent addresses applications calling for relatively thick layers where the core layer is between 0.01 and 0.09 inches (0.25 mm to 2.3 mm), with metal coatings of 0.002 to 0.0085 inches (50 to 210 micrometers).

U.S. Pat. No. 5,587,125 of Roychowdhury, assigned to Schneider (USA) Inc. is titled Non-Coextrusion Method of Making Multi-Layer Angioplasty Balloons, and teaches the fabrication of composite cylinders by fusing concentric tubes which then undergo blow molding.

U.S. Pat. No. 5,691,015 of Tsukamoto and Shimizu, assigned to Aicello Chemical Co. in Japan, is titled Composite Film Bags for Packaging, also teaches the fabrication of composite films, but those are used for making large bags suitable for storing chemical agents for agriculture where the outer film may be peeled off and the inner film is water soluble. When it is buried in soil, the film dissolves in water to release the agent.

U.S. Pat. No. 5,746,968 of Radisch, Jr., assigned to Interventional Technologies, Inc. is titled Method for Manufacturing a High Strength Angioplasty Balloon, and presents a method to increase the strength of a polymer balloon by special processing that results in directional orientation of the polymer chains using overstretching the balloon at an appropriate temperature. The method is claimed to preempt pinholes arising from the stretching steps. The balloon is not a composite.

U.S. Pat. No. 5,270,086 of Hamlin, assigned to Schneider (USA), with the title Multilayer Extrusion of Angioplasty Balloons, and presents a method to fabricate multiplayer balloons by co-extrusion, which have stable dimensions when stretched by pressurization.

U.S. Pat. No. 5,647,848 of Jorgensen, assigned to Meadox Medical, Inc., with the title High Strength Low Compliance Composite Balloon for Balloon Catheters, presents an elastomeric film that is restricted in its expansion under pressure by a constraining structure of filaments of high strength polymers such as Aramide, polyethylene or steel, carbon and so on. The result is a balloon strengthened against overexpansion by the helical filaments wound counter to one another.

Nylon 12 based nano-composites with low percentages of loading, on the order of a 2–5 percent, have achieved a significant (65%) decrease in the composite's flexural modulus and an even more significant (135%) increase in elongation. These properties seem to be needed for future angioplasty balloons as well as for stent deployment systems.

SUMMARY OF THE INVENTION

According to the present invention there is provided a method for making making, and a balloon catheter made by the method comprising a plastic tubing, a balloon fused to one end portion of said tubing, and said balloon comprising a carbon nanotube reinforced polymer, or a nanoclay reinforced polymer or a ceramic fiber reinforced polymer.

DESCRIPTION OF THE PREFERRED EMBODIMENTS

The method of fabrication of angioplasty balloons and similar devices for delivering stents and other forms of therapy with carbon nanotube enhanced, nanoclay enhanced or ceramic, alumina, enhanced composite materials will be described.

However, the second method to fabricate high strength composite balloons will be described first. The second or alternate method is based on the use of "nano-clays" occurring in natural clays. These clays contain platelets on a nanometric scale, which may be pretreated to bond strongly to the polymer matrix. Such nano-clays were described by Karl Kamena: An Emerging Family of Nanomer® Nano clays for the Plastics Industry (http://nanocor.com/tech_papers/nano_plastics.htm). Wet clay is a naturally plastic material. It comprises flat platelets which can slide on one another when wet, when the platelets are perfused with water. These platelets may be mixed with a monomer that forms a plastic material that can be molded or extruded into tubes and subsequently processed expanded into the desired balloon shape.

Fabrication

The process to disperse the nanoparticles in the host matrix may be aimed to be isotropic or oriented. Clay platelets improve, can slide with respect to one another, hence their elastic behavior is more pronounced in a plane parallel to the plates, while they are much more stiff in the orthogonal direction, as illustrated below:

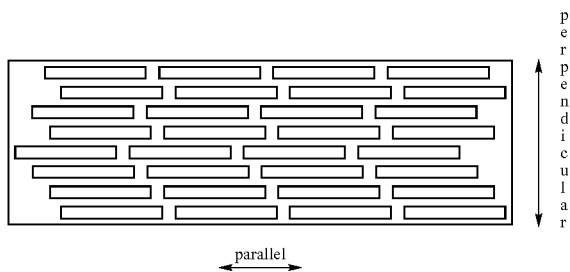

parallel

Such a structure is more responsive to tension in the parallel direction than in the perpendicular one. Random orientation of the platelets will provide more isotropic improvement in strength at a lesser magnitude. Depending on the adhesion between the plates in the matrix and the matrix the elastic behavior of the film that has parallel plates can be controlled. Therefore, there are at least three ways to influence the behavior of the composite: (1) by controlling the volume percent of platelets in the matrix; (2) by controlling the "wetting" of the platelets by the matrix; and (3) by controlling the orientation of the platelets within the matrix. Integration of these three properties will render an optimum material for the intended application. It is evident that one can make use of various known techniques to make clay nanoplatelets wettable. Nanocor, Inc. had concentrated on montmorillonite, a specific form of clay platelets, which can be modified to adhere to polymers. Montmorillonite is a "swelling" clay. It is able to absorb 20 to 30 times more water than its own starting volume. The layers are about 1 nm thick and its parallel dimensions are about 1000 times longer. Nanocor reports that when a small amount of water is added to montmorillonite (8–10% by weight) the platelets are spaced in "galleries" or layers with 0.3 to 0.5 nm spacing between them. U.S. Pat. No. 6,242,500 issued to Lan et al. on Jun. 5, 2001, discusses the use of onium ions to convert hydrophilic clay surfaces to hydrophobic one to enable one to enlarge the gallery height and bonding.

It is well known that phyllosilicates, such as smectite clays, e.g., sodium montmorillonite and calcium montmorillonite, can be treated with organic molecules, such as organic ammonium ions, to intercalate the organic molecules between adjacent, planar silicate layers, for bonding the organic molecules with a polymer, for intercalation of the polymer between the layers, thereby substantially increasing the interlayer (interlaminar) spacing between the adjacent silicate layers. The thus-treated, intercalated phyllosilicates, having interlayer spacings of at least about 10–20 .ANG. and up to about 100 Angstroms, then can be exfoliated, e.g., the silicate layers are separated, e.g., mechanically, by high shear mixing. The individual silicate layers, when admixed with a matrix polymer, before, after or during the polymerization of the matrix polymer, e.g., a polyamide—see U.S. Pat. Nos. 4,739,007; 4,810,734; and 5,385,776—have been found to substantially improve one or more properties of the polymer, such as mechanical strength and/or high temperature Exemplary prior art composites, also called "nanocomposites", are disclosed in published PCT application WO 93/04118 and U.S. Pat. No. 5,385,776, of Allied Signal, Inc. which disclose the admixture of individual platelet particles derived from intercalated layered silicate materials, with a polymer to form a polymer matrix having one or more properties of the matrix polymer improved by the addition of the exfoliated intercalate. As disclosed in WO 93/04118, the intercalate is formed (the interlayer spacing between adjacent silicate platelets is increased) by adsorption of a silane coupling agent or an onium cation, such as a quaternary ammonium compound, having a reactive group which is compatible with the matrix polymer. Such quaternary ammonium cations are well known to convert a highly hydrophilic clay, such as sodium or calcium montmorillonite, into an organophilic clay capable of sorbing organic molecules. A publication that discloses direct intercalation (without solvent) of polystyrene and poly(ethylene oxide) in organically modified silicates is "Synthesis and Properties of Two-Dimensional Nanostructures by Direct Intercalation of Polymer Melts in Layered Silicates", Richard A. Vaia, et al., "Chem. Mater"., 5:1694–1696(1993). Also, as disclosed in "Adv. Materials", 7, No. 2: (1985), pp, 154–156, "New Polymer Electrolyte Nanocomposites: Melt Intercalation of Poly(Ethylene Oxide) in Mica-Type Silicates", Richard A. Vaia, et al., poly(ethylene oxide) can be intercalated directly into Na-montmorillonite and Li-montmorillonite by heating to 80.degree. C. for 2–6 hours to achieve a d-spacing of 17.7 ANG. The intercalation is accompanied by displacing water molecules, disposed between the clay platelets, with polymer molecules. Apparently, however, the intercalated material could not be exfoliated and was tested in pellet form. It was quite surprising to one of the authors of these articles that exfoliated material could be manufactured in accordance with the teachings of the present invention.

The surface modification of the montmorillonite platelets and their integration into a polyamide or nylon polymer is an established art and not part of this disclosure. It was also described in considerable detail in "Synthesis and Characterisation of Thermoset-Clay Nanocomposites" by Xavier Kornman in a publication of "Lulea Tekniska Universitet", Sweden. The specific goal of this application is to specify the method of treatment of the platelets, the percentage of platelets within the matrix, the preferred method of compounding, the formation of the blank tubes which can be expanded into angiographic balloons for catheters.

The balloon forming process may begin with a polymer sheet of specific thickness that may be cut and fused into tubes whose wall thickness is considerably greater than necessary for making balloons for angioplasty catheters. Once the tubes are fused, they may be drawn down to the dimensions by well-established methods and formed into balloons by heating the thermoplastic tubes under internal pressure within a mold (blow molding). Another process will use an extruded thin wall tubing that is subsequently heat stretched in a controlled manner so as to further reduce the wall thickness to the desired dimensions. The stretched tube or parison is later blow molded into the desired balloon shape.

The method of creating composites with carbon nanotubes is based on the compounding of 0.20 to 20 percent of the available nanotubes in a polymer matrix. This may be achieved by dispersing the nanocomposite to the monomer followed by polymerization, or by dispersing the selected nanocomposite during conventional melt compounding. Again, tubes are formed with the nanotubes oriented primarily along the axis of the balloon.

To enhance the resistance of the balloon tangentially, the original compounding may be followed by rolling and stretching the polymer to orient the nanotubes in one direction and then forming the tubes such that the nanotubes are originally oriented tangentially in the wall of the tube:

Join Edge A to Edge B

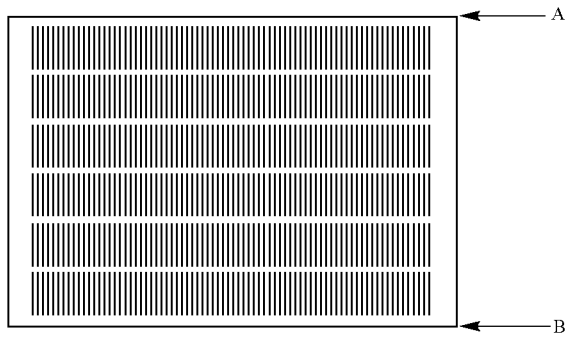

The tube is closed and sealed:

This tube is ready for being drawn out and then expanded. When it is in its final form, the orientation of the nanotubes should be somewhat randomized but oriented circumferentially on the average to increase the strength of the tube/balloon. An alternative process is to extrude the nanotube loaded polymer into thin wall tubes that will later be stretched and blow molded as required.

Naturally, the use of nanocomposites and nanotubes in thin tubular balloons is not limited to angioplasty in coronary vessels, but also to the general area of medical applications of balloons, including valvuloplasty, the minimally invasive repair of heart valves, angioplasty and stent development in peripheral vessels, deployment of stents especially in the coronary and carotid arteries, the repair of aneurysms by the insertion of balloons, even the possibility to insert balloons in the stomach for the purpose of reducing the subject's appetite (in the past the procedure failed on account of the balloon tearing and obstructing the intestinal path). All of these and other applications are intended to employ the teachings of the present invention.

I claim:

1. A balloon for use in a balloon catheter including a tubing, said balloon having a high strength for resisting bursting during over inflation, and said balloon comprising a blended nano-composite reinforced polymer matrix consisting essentially of a polymer selected from nylon 12 or PET and a nano composite selected from carbon nano-tubes or nano-ceramic fibers together with a lubricant to aid dispersion of the nano composite during blending of the matrix, said polymer and nano composite matrix being formed by controlling the volume or weight percent of nano composite in the matrix relative to the polymer such that the nano composite is between 0.20% and 20% by weight of the matrix and the polymer is between 80% and 99.80% of the matrix, by controlling the "wetting" of the nano composite in the matrix; and by controlling the orientation of the nano tubes or nano ceramic fibers within the matrix that is formed into a tube which is blow molded into said balloon wherein the nano-tubes or ceramic fibers are oriented along the axis of the balloon or tangentially in the wall of the tube.

2. The balloon of claim 1 being formed by extruding a polymer and nano composite matrix into a thin wall tube that is subsequently heat stretched in a controlled manner to further reduce a wall thickness of the tube to desired dimensions, followed by blow molding the stretched tube into a desired balloon shape.

3. The balloon of claim 1 wherein the polymer and nano composite matrix is formed by dispersing the nano composite to a monomer matrix followed by polymerization of the monomer and nano composite matrix.

4. The balloon of claim 1 wherein the polymer and nano composite matrix is formed by dispersing the selected nano composite in the matrix during melt compounding of the matrix.

5. The balloon of claim 1 being fused to one end of a tubing of a balloon catheter.

6. The balloon of claim 5 wherein said balloon comprises between 99.75 and 90.00% by weight polymer and between 0.25 and 10 by weight carbon nano-tubes.

7. The balloon of claim 6 wherein said balloon comprises approximately 3% by weight carbon nano-tubes.

8. The balloon of claim 5 wherein said nano composite is a nano-ceramic fiber.

9. The balloon of claim 8 wherein said balloon comprises between 99.75 and 90.00% by weight polymer and between 0.025 and 10.00% by weight nano-ceramic fibers.

10. The balloon of claim 9 comprising approximately 3% by weight nano-ceramic fibers.

11. The balloon of claim 8 wherein said nano-ceramic fibers are alumina fibers.

12. The balloon of claim 1 being formed by cutting a polymer and nano composite sheets of specific thickness, fusing the sheets into tubes whose wall thickness is considerably greater than necessary for making the balloon followed by drawing down the tubes formed by the laminated sheets to desired dimensions to form a thermoplastic tube and forming the balloon by heating the thermoplastic tube made from the laminated sheets under internal pressure within blow molding.

13. The balloon of claim 12 wherein the stretched tubes are formed with the nano-tubes or nano ceramic fibers oriented primarily along the axis of the balloon.

* * * * *